US00PP10418P

United States Patent [19]

Jessel, Jr.

[11] Patent Number: Plant 10,418

[45] Date of Patent: May 26, 1998

[54] CARNATION PLANT NAMED 'CFPC REMEMBRANCE'

[75] Inventor: Walter H. Jessel, Jr., Gonzales, Calif.

[73] Assignee: California Florida Plant Co., L.P., Salinas, Calif.

[21] Appl. No.: 711,033

[22] Filed: Sep. 10, 1996

[51] Int. Cl.[6] ..... A01H 5/00

[52] U.S. Cl. ..... Plt./70.3

[58] Field of Search ..... Plt./70.3, 70.5, Plt./70.2

*Primary Examiner*—Howard J. Locker

*Attorney, Agent, or Firm*—Christie, Parker & Hale.LLP

[57] ABSTRACT

A new variety of carnation plant very resistant to *F. oxysporum* and producing white flowers with a very pale pinkish cast.

1 Drawing Sheet

SUMMARY OF THE INVENTION

The present invention relates to a new and distinct variety of carnation plant which is a cross of the variety 'Koreno' as female parent and an undisclosed, undistributed seedling identified as 920258 as male parent. The varietal denomination of this new carnation is 'CFPC Remembrance'.

Among the novel combination of characteristics possessed by the new variety which distinguishes it are superior resistance to *F. oxysporum*, and *F. graminearum* and flowers of white with very pale pinkish cast. Among other differences, the new variety differs from its female and seed parents in flower coloration since 'Koreno', produces yellow flowers and the male parent produces light pink flowers.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypic expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Remembrance'.

Classification:

*Botanical.*—*Dianthus caryophyllus.*

*Commercial.*—Carnation, spray type.

Parentage:

*Female parent.*—'Koreno'.

*Male parent.*—920258.

1. Plant:
   - *Height.*—About 31 inches (first flowering).
   - *Growing habit.*—Herbaceous, semi-upright.
   - *Blooming habit.*—As a spray for cutting.
   - *Blooming season.*—Year round.
   - *Rooting time.*—About 18 days.
   - *Mutation prone.*—No.
   - *Disease resistance.*—Very good.
   - *Temperature tolerance.*—Wide range.
   - *Breaking action.*—Good, about 7 to 8 laterals per plant.
2. Foliage:
   - *Color.*—Upper side: Near 139A. Lower side: Near 136B.
   - *Size.*—About 5+ inches long, about 1/30 inch wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Near 138A.
3. Bud:
   - *Shape.*—Ovoid.
   - *Color.*—Near 145A.
   - *Length.*—About 1 inch.
   - *Diameter.*—About 4/10 inch.
4. Calyx:
   - *Number of sepals.*—About 6 to 7.
   - *Length.*—About 4/10 inch.
   - *Width.*—About 2/10 inch.
   - *Color.*—Outside — near 145B; base near 146D; top 1/3 near 147B Inside — near 146D.
5. Bloom:
   - *Shape.*—Round.
   - *Size.*—Diameter average: About 2 inches. Depth average: About 1 1/3 inches.
   - *Borne.*—Terminal sprays, about 3 to 5 blooms per spray, stem length approximately 31 inches.
   - *Color.*—General tonality: White with some pale pink impression. Upper side: White with a very pale pinkish cast (whiter than 36D). Lower side: Lighter than 36D. Center: White with a very pale pinkish cast (whiter than 36D). Outer petals: Near 36C.
   - *Keeping quality.*—Very good, about 2 to 3 weeks, petals do not drop.
   - *Fragrance.*—Slight.
6. Petals:
   - *Number.*—About 33 to 34.

*Outer petals.*—Length; About 1½ inches. Width: About ⅞ inches.

*Central petals.*—Length: About 1.3 inches. Width: About ⅝ inch.

*Texture.*—Smooth.

*Form.*—Fan shaped.

*Appearance.*—Shiny, smooth margin.

7. Reproductive organs:

*Stamens.*—Usually none, male sterile

*Anthers.*—About ⅛ inch, near 159D

*Filaments.*—About ⅜ inch, whiter than 155D.

*Pistil.*—Number: About 1. Color: Whiter than 155D. Length: About ¾ inch.

*Stigma.*—Number: About 3. Color: White.

*Ovary.*—Shape: Conical. Color: Base — near 155A. Body — near 155A. Apex — near 145B.

*Fertility.*—Female: Poor. Male: Sterile, anthers nonfunctional.

I claim:

1. A new and distinct variety of carnation plant substantially as shown and described.

* * * * *

PLT-274 SR
C5203 OR PP 010,418
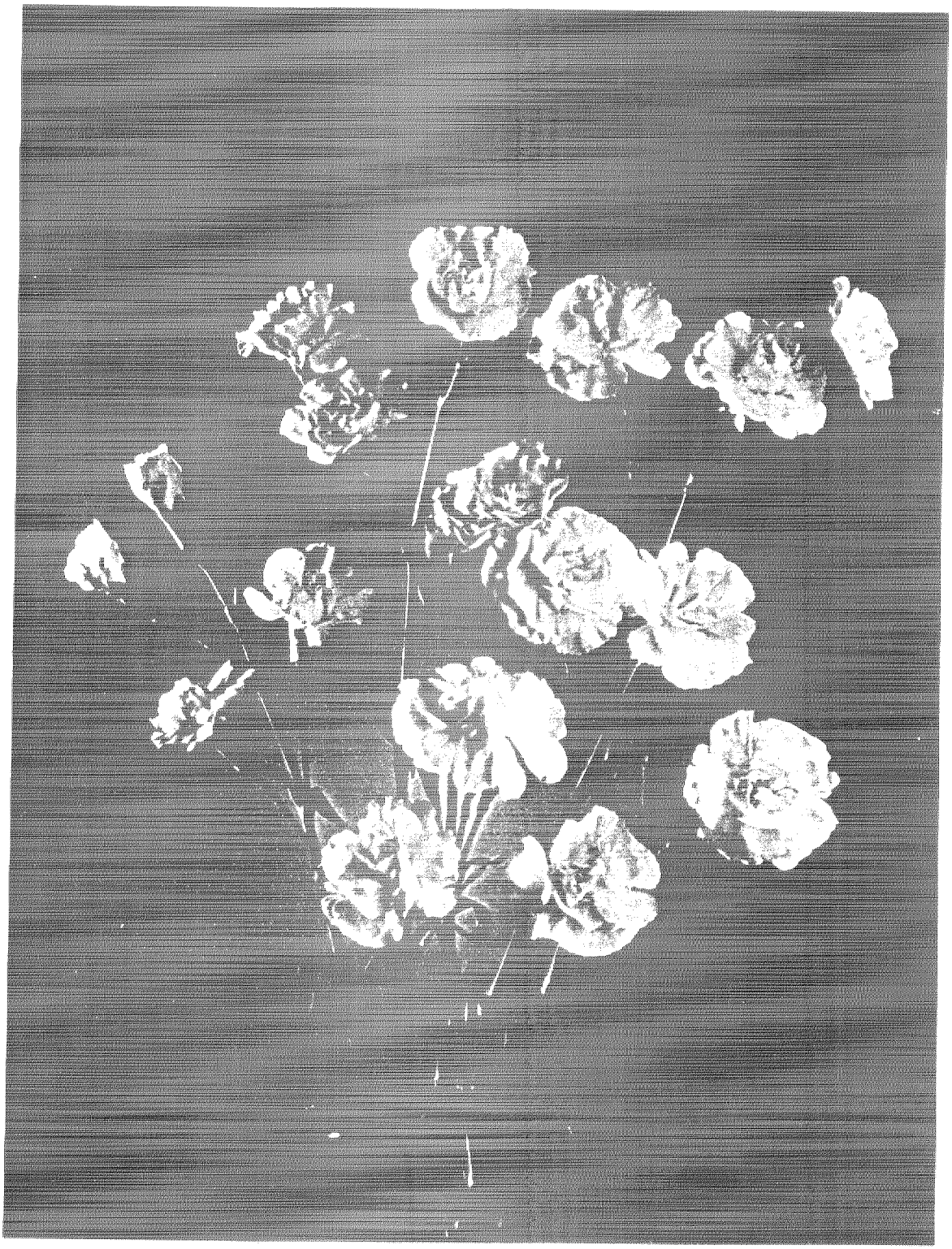

UNITED STATES PATENT AND TRADEMARK OFFICE

CERTIFICATE OF CORRECTION

PATENT NO. : Plant 10,418
DATED : May 26, 1998
INVENTOR(S) : Walter H. Jessel, Jr.

It is certified that error appears in the above-indentified patent and that said Letters Patent is hereby corrected as shown below:

Column 1, line 27, replace "DESCRIPTION OF THE VARIETY" with -- DESCRIPTION OF THE NEW VARIETY --.
Column 2, line 15, change "⅓0 inch" to -- ⅓ inch --.

Signed and Sealed this

Third Day of August, 1999

*Attest:*

*Attesting Officer*

Q. TODD DICKINSON

*Acting Commissioner of Patents and Trademarks*